(12) United States Patent
Im et al.

(10) Patent No.: US 9,481,963 B2
(45) Date of Patent: Nov. 1, 2016

(54) MANUFACTURING METHOD OF CARBOXYMETHYL CELLULOSE NONWOVEN FABRIC AND USE OF CARBOXYMETHYL CELLULOSE NONWOVEN FABRIC MANUFACTURED THEREBY

(71) Applicants: Jung Nam Im, Cheonan-si (KR); Song Jun Doh, Suwon-si (KR); Dae Young Lim, Yongin-si (KR); Ji Yun Lee, Incheon (KR)

(72) Inventors: Jung Nam Im, Cheonan-si (KR); Song Jun Doh, Suwon-si (KR); Dae Young Lim, Yongin-si (KR); Ji Yun Lee, Incheon (KR)

(73) Assignee: Korea Institute of Industrial Technology, Cheonan-si (KR)

( * ) Notice: Subject to any disclaimer, the term of this patent is extended or adjusted under 35 U.S.C. 154(b) by 0 days.

(21) Appl. No.: 14/348,733

(22) PCT Filed: Oct. 23, 2013

(86) PCT No.: PCT/KR2013/009471
§ 371 (c)(1),
(2) Date: Mar. 31, 2014

(87) PCT Pub. No.: WO2014/092328
PCT Pub. Date: Jun. 19, 2014

(65) Prior Publication Data
US 2016/0002859 A1    Jan. 7, 2016

(30) Foreign Application Priority Data
Dec. 10, 2012 (KR) .......... 10-2012-0143109

(51) Int. Cl.
| | | |
|---|---|---|
| *D21H 27/00* | (2006.01) | |
| *D21H 13/00* | (2006.01) | |
| *D21H 13/04* | (2006.01) | |
| *A61L 15/28* | (2006.01) | |
| *D21H 11/20* | (2006.01) | |

(52) U.S. Cl.
CPC ............ *D21H 27/007* (2013.01); *A61L 15/28* (2013.01); *D21H 5/141* (2013.01); *D21H 11/20* (2013.01); *D21H 13/04* (2013.01); *A61L 2300/80* (2013.01)

(58) Field of Classification Search
CPC ............................ D21H 27/00; D21H 11/20
USPC ...................................... 162/157.6
See application file for complete search history.

(56) References Cited

U.S. PATENT DOCUMENTS

| | | | | |
|---|---|---|---|---|
| 6,075,177 A * | 6/2000 | Bahia | ............... | A61F 13/00008 |
| | | | | 536/56 |
| 8,039,683 B2 * | 10/2011 | Qin | ......... | A61F 13/53 |
| | | | | 604/367 |
| 8,828,424 B2 * | 9/2014 | Bray | ....... | A61L 15/28 |
| | | | | 424/445 |

FOREIGN PATENT DOCUMENTS

| | | |
|---|---|---|
| EP | 0 680 344 B1 | 4/1998 |
| JP | 2000 256958 A | 9/2000 |
| JP | 2007 197862 A | 8/2007 |
| JP | 2010 284216 A | 12/2010 |
| KR | 2008 0075627 A | 8/2008 |

* cited by examiner

*Primary Examiner* — Mark Halpern
(74) *Attorney, Agent, or Firm* — Reinhart Boerner Van Deuren P.C.

(57) ABSTRACT

The present invention relates to a manufacturing method of a carboxymethyl cellulose nonwoven fabric which includes the carboxymethylation of cellulose fibers and the subsequent paper-making process to prepare a carboxymethyl cellulose nonwoven fabric. Comparing with the conventional method involving carboxymethylation of a nonwoven fabric, the method of the present invention has convenience and easiness of the process and thus enables production on a large scale. Further, the carboxymethyl cellulose nonwoven fabric manufactured by the present invention is susceptible to gelation upon contact with body fluids or water and thus useful as a medical nonwoven fabric or a mask pack.

9 Claims, 4 Drawing Sheets

MANUFACTURING METHOD OF CARBOXYMETHYL CELLULOSE NONWOVEN FABRIC AND USE OF CARBOXYMETHYL CELLULOSE NONWOVEN FABRIC MANUFACTURED THEREBY

TECHNICAL FIELD

The present invention relates to a manufacturing method of carboxymethyl cellulose nonwoven fabric and the use of the wet-laid carboxymethyl cellulose nonwoven fabric manufactured thereby and, more particularly to, a manufacturing method of a carboxymethyl cellulose nonwoven fabric and the use of the carboxymethyl cellulose nonwoven fabric, which method includes the carboxymethylation of cellulose fibers and followed by subsequent paper-making process. According to the method of the present invention, it is possible to make a nonwoven fabric that is superior in uniformity to the conventional nonwoven fabric prepared by carboxymethylation of conventional nonwoven fabric made of cellulose, and carboxymethylated cellulose nonwoven fabric can be produced on a large scale because of convenience and easiness of the process. And the carboxymethyl cellulose nonwoven fabric manufacture by the method of the present invention can be gelled upon contact with body fluids or water and thus useful as a medical nonwoven fabric or a material for mask pack.

BACKGROUND ART

Nonwoven fabrics are defined as planar fiber structure prepared by entangling any kind of fibers such as natural fibers, synthetic fibers, glass fibers, metal fibers, etc., into the form of a sheet-like web under the consideration of individual fiber characteristics, and then binding them either mechanically or physically.

In recent years, nonwoven fabrics are widely used in industry and surrounding of life. As the uses, features and functions of nonwoven fabrics begin to be known to the end users, there have been created a variety of uses of the nonwoven fabrics.

Particularly, out of natural fibers, cellulose fibers are an most abundant bio-resource in the earth, and used by mankind for several thousand years as a low-cost and renewable material that can be repeatedly recycled according to the natural system of generation, degradation and consumption. As such cellulose fibers are considered as an energy and food resource, there have been actively made technical developments for making the use of the cellulose components of plants. Moreover, a recent increase in the need for ecofriendly polymer materials has led to flourishing studies on the cellulose as a substitute for all kinds of functional polymer material and a polymer resource used in industry.

The third hydroxyl group of the cellulose molecule is so reactive as to participate in a chemical reaction such as esterification, nitration, or oxidation. Hence, the cellulose fibers can be transformed into a biocompatible material in a wide range of biomedical applications.

In regards to this, knitted products using oxidized cellulose fiber prepared by oxidization of cellulose are excellent in adhesion to the curved organs and tissues and therefore commercially available as anti-adhesion barriers. But, these products have such a large pore size as to be readily permeable to various cells, blood proteins, or the like, consequently with low efficiency as a separation membrane. Also, there are commercially available film-like products using carboxymethyl cellulose (CMC) prepared by carboxymethylation of cellulose. The film-like products, which have no micro pores, are poor in adhesion and too stiff to handle with ease.

To solve these problems, there has been made an attempt to provide a method of preparing nonwoven fabrics from nanofibers using electrospinning. A representative one of the direct cellulose electrospinning methods is the NMMO (4-methylmorpholine N-oxide) spinning method, which had the difficulty in producing nano-sized fibers and, even when producing fibers in nano size, fails to laminate nonwoven fabrics because of the characteristic of the NMMO solution that tends to solidify at temperature below 80° C.

In an attempt to overcome this problem, Korean Patent Laid-Open No. 2008-0075627 discloses a method of preparing cellulose nanofibers that includes electrospinning cellulose acetate and then carrying out deacetylation of the electrospun cellulose acetate with potassium hydroxide and ethanol. But, the cited patent has no mention about nonwoven fabrics that uses oxidized cellulose and thus can be used as a hemostatic dressing or an anti-adhesion barrier with good biodegradability.

Thus, there is a need for preparation of carboxymethyl cellulose nonwoven fabrics consisting of nanofibers that acts as a separation membrane, readily permeable by various cells, blood proteins, or the like, and is applicable to medical materials such as a hemostatic dressing or an anti-adhesion barrier with good biodegradability.

Another method for preparing cellulose nonwoven fabric includes formation of a wet-laid nonwoven fabric by the paper-making process and subsequent carboxymethylation.

FIG. 1 illustrates a process of preparing a wet-laid nonwoven fabric using the paper-making process, where the method includes the step of (1) pulverizing fibers to obtain pulped fibers, (2) when necessary, repeatedly dispersing the pulped fibers with water used as a paper-making solvent, (3) eliminating water and applying the pulped fibers in the form of a sheet on a paper-making wire or screen 31 using a vacuum pump 32, (4) obtaining a wet-laid nonwoven fabric in the form of a sheet using a pressure roll, and (5) winding the wet-laid nonwoven fabric. The wet-laid nonwoven fabric sheet thus obtained is formed by dispersing extremely short fibers, for example, 0.1 to 10 mm long in water in order to secure uniform dispersion of the fibers and thus superior in uniformity to dry-laid nonwoven fabrics. When carboxymethylated, the wet-laid nonwoven fabric has low oxidization efficiency, leading to the difficulty of the process.

In an attempt to apply a wet-laid nonwoven fabric prepared by the paper-making process to medical use purposes, the inventors of the present invention have contrived a method of carboxymethylating cellulose fibers and then preparing a wet-laid nonwoven fabric using the paper-making process, where the carboxymethyl cellulose wet-laid nonwoven fabric thus obtained has good uniformity and offers convenience and easiness in the process using the cellulose fibers commercially available, thereby completing the present invention.

DISCLOSURE OF INVENTION

Technical Problem

It is therefore an object of the present invention to provide a manufacturing method of preparing a carboxymethyl cellulose nonwoven fabric with good uniformity.

It is another object of the present invention to provide a medical nonwoven fabric for a water-absorption material using the carboxymethyl cellulose nonwoven fabric manufactured by the method.

It is still another object of the present invention to provide a mask pack using the carboxymethyl cellulose nonwoven fabric manufactured by the aforementioned method.

Technical Solution

To achieve the objects of the present invention, there is provided a wet-laid manufacturing method of a carboxymethyl cellulose nonwoven fabric that includes treating cellulose fibers chemically in a solvent to prepare carboxymethyl cellulose fibers; disentangling and mixing the carboxymethyl cellulose fibers in a paper-making solution comprising an alcohol solvent; and eliminating the solvent.

The method of the present invention may further include, after elimination of the solvent, performing a pressing process using calendering.

In the preparation method of the present invention, the cellulose fibers may be selected from the group consisting of viscos rayon fiber, cotton fiber, and Lyocell fiber.

Preferably, the carboxymethyl cellulose fibers obtained in the method of the present invention may have a length of 0.1 to 10 mm.

The alcohol solvent used in the method of the present invention may be selected from the group consisting of ethanol, methanol, and propanol. The alcohol solvents may be used alone or a mixture thereof.

The present invention also provides a medical nonwoven fabric for a water-absorption material using the carboxymethyl cellulose nonwoven fabric manufactured by the method, wherein the carboxymethyl cellulose nonwoven fabric is gelated upon contact with body fluid.

Further, the medical nonwoven fabric of the present invention may enhance the convenience of operation or the visibility in use by dyeing the carboxymethyl cellulose nonwoven fabric with a biocompatible dye or pigment. The carboxymethyl cellulose nonwoven fabric may be further coated by an antibacterial material.

Furthermore, the present invention provides a mask pack using the carboxymethyl cellulose nonwoven fabric with good uniformity as obtained from the method.

Advantageous Effects

The present invention provides a manufacturing method of a nonwoven fabric by the carboxymethylation of cellulose fibers followed by subsequent paper-making process to prepare a nonwoven fabric. The carboxymethyl cellulose nonwoven fabric manufactured by the present invention is superior in uniformity to the conventional nonwoven fabric prepared by carboxymethylation of nonwoven fabric itself, and, the method of the present invention is proper to a large scale production because the carboxylmethylation of fiber is easier and more convenient than the carboxymethylation nonwoven fabric.

The carboxymethyl cellulose nonwoven fabric manufactured by the method of the present invention is susceptible to gelation upon contact with body fluids or water and thus useful as a material for medical nonwoven fabric or mask pack.

BRIEF DESCRIPTION OF ACCOMPANYING DRAWINGS

DETAILED DESCRIPTION OF THE PRESENT INVENTION

Hereinafter, the present invention will be described in detail.

The present invention provides a manufacturing method of a carboxymethyl cellulose nonwoven fabric by the carboxymethylation of cellulose fibers and the subsequent paper-making process.

More specifically, the present invention provides an wet-laid manufacturing method of a carboxymethyl cellulose nonwoven fabric that includes (1) chemical treating cellulose fibers to prepare carboxymethyl cellulose fibers and (2) disentangling and mixing the carboxymethyl cellulose fibers in a paper-making solution composed of an alcohol solvent and eliminating the solvent.

Figure 1:
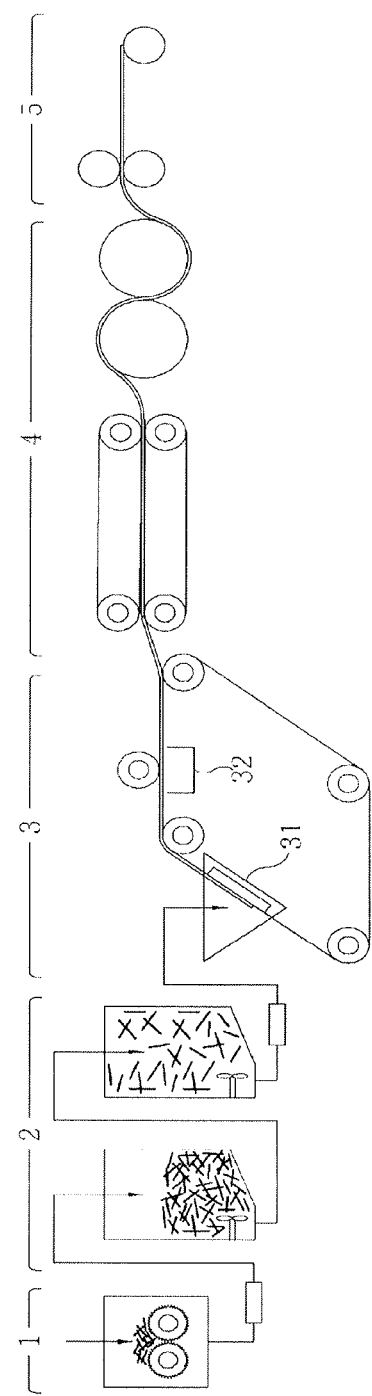
FIG. 1 illustrates a conventional process for preparing a nonwoven fabric using the paper-making process.

The conventional cellulose nonwoven fabric is obtained by preparing a nonwoven fabric according to the paper-making process of FIG. 1 and then performing a subsequent oxidization process to form the final product. But, the conventional process of carboxymethylating the nonwoven fabric has many demerits such as difficulties in keeping the shape of the nonwoven fabric, permeating the solvent to narrow space between nonwoven fabrics or fibers, and said demerits readily leads to low oxidization efficiency and poor uniformity of prepared nonwoven fabrics.

Further, when preparing a nonwoven fabric using the carboxymethyl cellulose fibers by the needle punching process, the brittleness of carboxymethyl cellulose fibers makes the process difficult to perform, renders the production rate too slow, and ends up with failure to produce a nonwoven fabric in the form of a thin layer.

On the other hand, the manufacturing method of carboxymethyl cellulose nonwoven fabric according to the present invention involves the dispersion of cellulose fibers in a solvent and the subsequent carboxymethylation process, making the carboxymethylation reaction occurring uniformly and securing high oxidization efficiency. Conventional wet-laid manufacturing method of nonwoven fabrics use water as a paper-making solvent. But, carboxymethyl cellulose fibers are susceptible to gelation upon contact with water and thus difficult to prepare by the conventional paper-making process. On the other hand, the carboxymethyl cellulose nonwoven fabric according to the present invention is prepared using alcohol as a paper-making solvent. This leads to good uniformity and improves the efficiency of the process, making the production on a large scale possible.

In the step (1) of the manufacturing method of the present invention, the cellulose fibers to be carboxymethylated may be any one selected from the group consisting of viscos rayon fiber, cotton fiber, and Lyocell fiber. In the examples of the embodiments of the present invention, the method for carboxymethyl cellulose nonwoven fabric uses viscos rayon fibers or cotton fibers. But, the cellulose fibers are not specifically limited to those fibers.

The carboxymethylation process of the step (1) is a process of treating cellulose fibers with an alkali and then reacting them with monochloroacetic acid to form carboxymethyl cellulose where the degree of substitution is 0.3 or greater.

The step (2) of the method of the present invention is a wet-laid process of preparing a nonwoven fabric according to the paper-making process, and includes disentangling and mixing the carboxymethyl cellulose fibers in a paper-making solution composed of an alcohol solvent and eliminating the solvent to dry the cellulose fibers.

In the step (2) of the present invention, the paper-making solution uses an alcohol as a solvent, because carboxymethyl cellulose is susceptible to gelation upon contact with water.

In the examples of the present invention, the paper-making solution comprises an ethanol solvent, but not limited to it. Preferably, the solvent of the paper-making solution is any one selected from the group consisting of ethanol, methanol, propanol, and mixtures thereof.

The carboxymethylated cellulose fibers obtained in the method of the present invention are preferably 0.1 to 10 mm long. When the fibers are shorter than 0.1 mm, the bonding force between the fibers reduces to deteriorate the shape forming stability of the nonwoven fabric. When the fibers are longer than 10 mm, it is difficult to disperse the fibers uniformly in the paper-making solution.

A first preferred embodiment of the present invention prepared from the above-described manufacturing method for carboxymethyl cellulose nonwoven fabric provides a carboxymethyl cellulose nonwoven fabric using the viscos rayon fibers prepared in Example 1; and a second preferred embodiment of the present invention provides a carboxymethyl cellulose nonwoven fabric using cotton fibers prepared in Example 2.

Figure 2:
FIG. 2 is an image showing the cross-section of a carboxymethyl cellulose nonwoven fabric using viscos rayon fibers according to Example 1 of the present invention.
Figure 3:
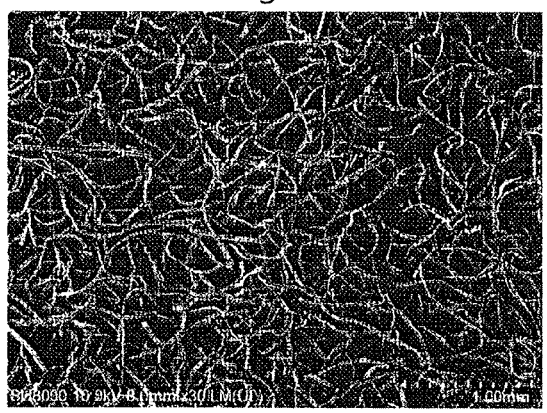
FIG. 3 is an image showing the surface of the carboxymethyl cellulose nonwoven fabric using viscos rayon fibers in FIG. 2.

In this regard, FIGS. 2 and 3 are images showing the cross-section and the surface of the carboxymethyl cellulose nonwoven fabric using the viscos rayon fibers prepared in Example 1, respectively. It can be seen from the images that the carboxymethyl cellulose nonwoven fabric using the viscos rayon fibers is a porous thin-film type nonwoven fabric having micro pores, with carboxymethyl cellulose fibers uniformly dispersed. The micro pores can induce capillary actions to control the rate of gelation to be faster.

Furthermore, the manufacturing method of the present invention may further include a pressing process according to the calendering process after removal of the solvent in the step (2).

Figure 4:
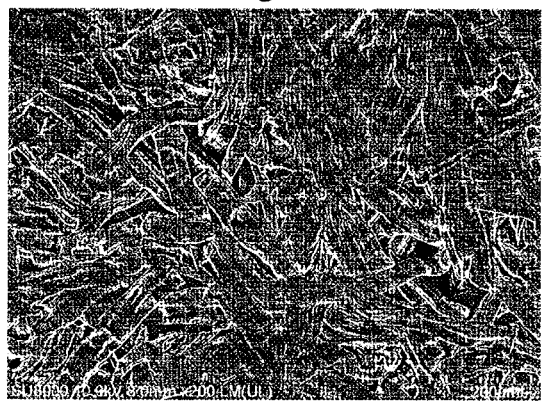
FIG. 4 is an image showing the surface of the carboxymethyl cellulose nonwoven fabric using viscos rayon fibers after calendering in Example 1 of the present invention.

FIG. 4 is an image showing the surface of the carboxymethyl cellulose nonwoven fabric using the viscos rayon fibers prepared in Example 1 after the calendering process. It can be seen from the image that the average pore size of the nonwoven fabric after the calendering process is smaller than that of the nonwoven fabric before the calendering process (FIG. 3).

In then method of the present invention, the average pore size of the carboxymethyl cellulose nonwoven fabric can be easily controlled, and further, the sheet strength of nonwoven fabric can be improved by the calendering process, therefore, the thickness of the nonwoven fabric can be thinner.

Moreover, the carboxymethyl cellulose nonwoven fabric manufactured by the method of the present invention can have strong sheet strength and good uniformity because of the carboxymethylation reaction uniformly performed. Further, the carboxymethyl cellulose nonwoven fabric is susceptible to gelation upon contact with water, and thus applicable to a medical nonwoven fabric as a water absorption material.

In this regard, the carboxymethyl cellulose nonwoven fabric manufactured by the method of the present invention is useful as a medical nonwoven fabric applicable to any one selected from the group consisting of an anti-adhesion barrier, a wound dressing, and a hemostatic dressing.

Hereinafter, a description will be given as to the case that the carboxymethyl cellulose nonwoven fabric of the present invention is used for an anti-adhesion barrier, which is not intended to limit the present invention.

Conventionally, anti-adhesion barriers in the form of a knit or a film are commercially available. The knit type anti-adhesion barrier has extremely large pores between fibers to possibly create a region that cannot be blocked by gelation. Further, such a knit type anti-adhesion barrier needs to use long filaments in order to be prepared to the form of a knit.

Contrarily, the anti-adhesion barrier using the carboxymethyl cellulose nonwoven fabric fabricated by the method of the present invention can secure a sheet strength strong enough and is controllable in regards to the micro pore size, in comparison with the conventional knit type anti-adhesion barrier. That is, the carboxymethyl cellulose nonwoven fabric used as the medical nonwoven fabric of the present invention is preferably designed to have pores having a pore size of 1 to 500 µm. In this regard, the pore size of the carboxymethyl cellulose nonwoven fabric less than 1 µm deteriorates the function of the micro pores between the fibers, retarding the solution/water absorption rate. In contrast, the pore size of the carboxymethyl cellulose nonwoven fabric greater than 500 µm renders the pores between the fibers extremely large even when the gelation of the material by water occurs, readily deteriorating the blocking properties.

Further, the present invention involves dyeing the carboxymethyl cellulose wet-laid nonwoven fabric with a biocompatible dye or pigment. This can enhance the operational convenience or the in-use visibility of the medical nonwoven fabric using the carboxymethyl cellulose nonwoven fabric.

In this regard, the dye or pigment may be selected out of substances harmless to human body as known in the related art. The dye or pigment is preferably selected to take a complementary color of the blood in order to make it easily noticeable whether or where the medical nonwoven fabric is located in the organ.

Further, at the present invention, an antibacterial substance can be added to the carboxymethyl cellulose nonwoven fabric to enhance the anti-infective performance of the medical nonwoven fabric using the carboxymethyl cellulose nonwoven fabric. In this regard, the antibacterial substance may be any one selected from the antibacterial substances harmless to human body as known in the related art and may include silver, silver compounds, trichloric acid, biguanide compounds, methylene blue, and so forth.

Furthermore, the present invention provides a mask pack using the carboxymethyl cellulose nonwoven fabric produced by the aforementioned manufacturing method.

Figure 5:
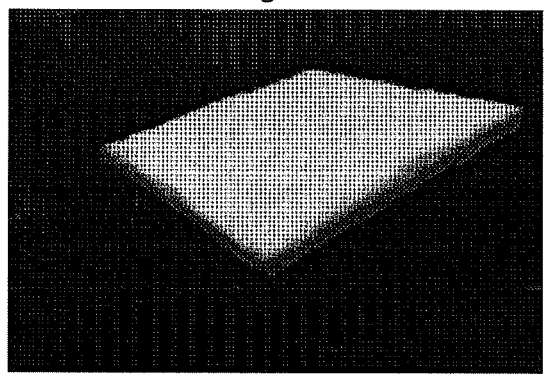
FIG. 5 is an optical image of a carboxymethyl cellulose nonwoven fabric using cotton fibers according to Example 2 of the present invention.
Figure 6:
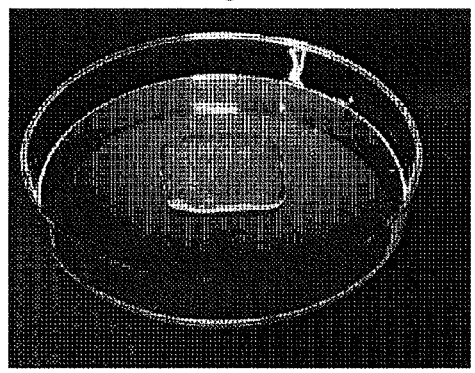
FIG. 6 is an optical image of the carboxymethyl cellulose nonwoven fabric using cotton fibers of FIG. 5 in contact with water.
Figure 7:
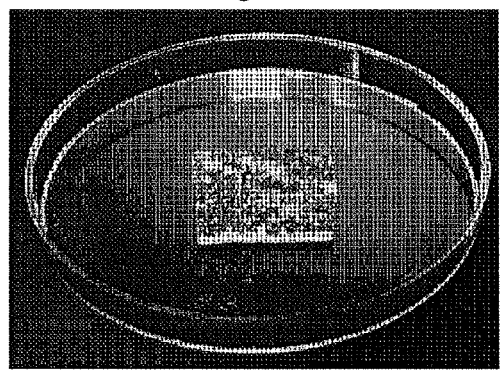
FIG. 7 is an optical image of a carboxymethyl cellulose nonwoven fabric using a cotton fabric according to Comparative Example 1 of the present invention in contact with water.

FIG. 5 is an optical image of a carboxymethyl cellulose nonwoven fabric using cotton fibers according to Example 2 of the present invention. FIG. 6 is an optical image of the carboxymethyl cellulose nonwoven fabric using cotton fibers of FIG. 5 in contact with water. The results of observation show what the nonwoven fabrics look like after gelation upon contact with water. Contrarily, FIG. 7 relates to a carboxymethyl cellulose nonwoven fabric using a cotton fabric according to Comparative Example 1. It can be seen from FIG. 7 that the carboxymethyl cellulose nonwoven fabric obtained by preparing a nonwoven fabric and then carboxymethylating it according to the conventional method has a region partly without gelation upon contact with water.

BEST MODE FOR CARRYING OUT THE INVENTION

Hereinafter, the present invention will be described in further detail with reference to the examples.

The examples are given to illustrate the present invention in further detail and not intended to limit the scope of the present invention.

Example 1

Manufacturing Carboxymethyl Cellulose Nonwoven Fabric Using Viscos Rayon Fiber

Step 1: Carboxymethylation 400 g of 25% sodium hydroxide solution is added to a mixed solution prepared by mixing 1,350 ml of 2-propanol and 1,350 ml of ethanol, and the resultant solution is stirred to prepare an alkali solution. 30 g of viscos rayon fiber is added to the alkali solution, and after 20-minute agitation, an alkali-treated viscos rayon fiber is prepared.

Subsequently, 26.3 g of monochloroacetic acid (MCA) is dissolved in a mixed solution consisting of 1,350 ml of 2-propanol and 1,350 ml of ethanol as maintained at 70° C. to prepare an esterifying solution. The alkali-treated viscos rayon fiber is put into the solution, which is then stirred for 30 minutes.

After completion of the reaction, the carboxymethyl cellulose fiber is put in 99.5% methanol for washing, neutralized with acetic acid and the stirred for 10 minutes. The carboxymethyl cellulose fiber is washed with 95% ethanol for 10 minutes and then sequentially with 99.5% methanol and 95% ethanol, each for 10 minutes. The washed carboxymethyl cellulose (CMC) fiber is dried at 50° C.

Step 2: Manufacturing Nonwoven Fabric by Paper-Making 2.25 g of the carboxymethyl cellulose (CMC) fiber prepared in Step 1 in 5 L of 95% ethanol is sufficiently mixed with a paper-making solution using ethanol as a solvent. Subsequently, a hand sheet former is used to eliminate the ethanol used as a solvent to prepare a carboxymethyl cellulose wet-laid nonwoven fabric (100 g/m$^2$). The nonwoven fabric thus obtained is dried at 50° C.

Step 3: The nonwoven fabric prepared in Step 2 is subjected to the calendering process under the pressure of 200 psi at 90° C.

Example 2

Preparation of Carboxymethyl Cellulose Nonwoven Fabric Using Cotton Fiber

Step 1: Carboxymethylation 400 g of 25% sodium hydroxide solution is added to a mixed solution prepared by mixing 1,350 ml of 2-propanol and 1,350 ml of ethanol, and the resultant solution is stirred for 20 minutes to prepare an alkali solution. 30 g of cotton fiber is added to the alkali solution, and after 20-minute agitation, an alkali-treated cotton fiber is prepared.

Subsequently, 87 g of monochloroacetic acid (MCA) is dissolved in a mixed solution consisting of 1,350 ml of 2-propanol and 1,350 ml of ethanol as maintained at 70° C. to prepare an esterifying solution. The alkali-treated cotton fiber is put into the solution, which is then stirred for 30 minutes.

After completion of the reaction, the carboxymethyl cellulose fiber is put in 99.5% methanol for washing, neutralized with acetic acid and the stirred for 10 minutes. The carboxymethyl cellulose fiber is washed with 95% ethanol for 10 minutes and then sequentially with 99.5% methanol and 95% ethanol, each for 10 minutes. The washed carboxymethyl cellulose (CMC) fiber is dried at 50° C.

Step 2: Manufacturing Nonwoven Fabric by Paper-Making 6.75 g of the carboxymethyl cellulose (CMC) fiber prepared in Step 1 in 5 L of 95% ethanol is sufficiently mixed with a paper-making solution using ethanol as a solvent. Subsequently, a hand sheet former is used to eliminate the ethanol used as a solvent to prepare a carboxymethyl cellulose nonwoven fabric (300 g/m$^2$). The nonwoven fabric thus obtained is dried at 50° C.

Comparative Example 1

Manufacturing Carboxymethyl Cellulose Nonwoven Fabric Using Cotton Fiber

A nonwoven fabric (50 g/m$^2$) is prepared, and then a carboxymethyl cellulose nonwoven fabric is prepared under the conditions of carboxymethylation given in Example 2. Firstly, 400 g of 25% sodium hydroxide solution is added to a mixed solution prepared by mixing 1,350 ml of 2-propanol and 1,350 ml of ethanol, and the resultant solution is stirred to prepare an alkali solution. 30 g of the nonwoven fabric using cotton fiber is added to the alkali solution, and after 20-minute agitation, an alkali-treated nonwoven cotton fiber is prepared.

Subsequently, 87 g of monochloroacetic acid (MCA) is dissolved in a mixed solution consisting of 1,350 ml of 2-propanol and 1,350 ml of ethanol as maintained at 70° C. to prepare an etherifying solution. The alkali-treated cotton nonwoven fiber is put into the solution, which is then stirred for 30 minutes.

After completion of the reaction, the carboxymethyl cellulose nonwoven fiber is put in 99.5% methanol for washing, neutralized with acetic acid and the stirred for 10 minutes. The carboxymethyl cellulose nonwoven fiber is washed with 95% ethanol for 10 minutes and then sequentially with 99.5% methanol and 95% ethanol, each for 10 minutes. The washed carboxymethyl cellulose (CMC) nonwoven fiber is dried at 50° C.

INDUSTRIAL APPLICABILITY

As described above, the present invention provides a method for preparing a carboxymethyl cellulose wet-laid nonwoven fabric by the carboxymethylation of cellulose fibers and the subsequent paper-making process.

The preparation method of the present invention includes treating cellulose fibers chemically in a solvent to prepare carboxymethyl cellulose fibers and then disentangling and mixing the carboxymethyl cellulose fibers in a paper-making solution composed of an alcohol solvent, followed by elimination of the solvent, to prepare a nonwoven fabric that not only has good uniformity but also can be produced on a large scale because of the convenience of the process using the existing cellulose fibers commercially available and the easiness of the process.

As the carboxymethyl cellulose nonwoven fabric manufactured by method of the present invention is susceptible to gelation upon contact with body fluids or water, the present invention also provides the use of the carboxymethyl cellulose nonwoven fabric as a medical nonwoven fabric or a mask pack.

While the present invention has been particularly illustrated and described with reference to preferred embodiments thereof, various modifications or changes can be made without departing from the scope of the present invention.

1: Pulverization
2: Dispersion
3: Bonding in sheet form
4: Sheet formation
31: Paper-making wire or screen
32: Vacuum pump
5: Winding

The invention claimed is:

1. A manufacturing method of a wet-laid carboxymethyl cellulose nonwoven fabric having a pore size of 1 to 500 μm, comprising the steps of:
   treating cellulose fibers chemically to prepare carboxymethyl cellulose fibers;
   disentangling and mixing the carboxymethyl cellulose fibers in a paper-making solution comprising an alcohol solvent, wherein the alcohol solvent is selected from the group consisting of ethanol, methanol, propanol, and mixtures thereof; and
   eliminating the alcohol solvent.

2. The method as claimed in claim 1, further comprising the step of performing a pressing process using calendering after eliminating the solvent.

3. The method as claimed in claim 1, wherein the cellulose fibers are selected from the group consisting of viscos rayon fiber, cotton fiber, and Lyocell fiber.

4. The method as claimed in claim 1, wherein the carboxymethyl cellulose fibers have a length of 0.1 to 10 mm.

5. A medical nonwoven fabric for a water-absorption material comprising:
   a porous wet-laid carboxymethyl cellulose nonwoven fabric having a pore size of 1 to 500 μm, wherein the pore size can induce capillary actions to control the rate of gelation such that the wet-laid carboxymethyl cellulose nonwoven fabric is entirely gelated upon contact with body fluid.

6. The medical nonwoven fabric as claimed in claim 5, wherein the water-absorption material is selected from the group consisting of an anti-adhesion barrier, a wound dressing, and a hemostatic dressing.

7. The medical nonwoven fabric as claimed in claim 5, wherein the carboxymethyl cellulose nonwoven fabric is dyed with a biocompatible dye or pigment.

8. The medical nonwoven fabric as claimed in claim 5, wherein the carboxymethyl cellulose nonwoven fabric is further coated with an antibacterial material.

9. A mask pack comprising:
   a porous wet-laid carboxymethyl cellulose nonwoven fabric having a pore size of 1 to 500 μm, wherein the pore size can induce capillary actions to control the rate of gelation such that the wet-laid carboxylmethyl cellulose nonwoven fabric is entirely gelated upon contact with body fluid.

* * * * *